United States Patent [19]
Herbert

[11] Patent Number: 6,096,042
[45] Date of Patent: Aug. 1, 2000

[54] DRIVER

[76] Inventor: Timothy James Herbert, 159 Whale Beach Road, Whale Beach, NSW 2107, Australia

[21] Appl. No.: 09/101,207
[22] PCT Filed: Dec. 23, 1996
[86] PCT No.: PCT/AU96/00833
 § 371 Date: Mar. 2, 1999
 § 102(e) Date: Mar. 2, 1999
[87] PCT Pub. No.: WO97/24991
 PCT Pub. Date: Jul. 17, 1997

[30] Foreign Application Priority Data

Jan. 4, 1996 [AU] Australia ............................. PN 7419

[51] Int. Cl.$^7$ ................................................. A61B 17/00
[52] U.S. Cl. ................................................. 606/80; 606/79
[58] Field of Search ................................. 606/80, 79, 81, 606/96, 167, 170, 172, 173, 180, 97, 98

[56] References Cited

U.S. PATENT DOCUMENTS

| | | | |
|---|---|---|---|
| 2,267,008 | 12/1941 | Zimmer | 211/69 |
| 2,526,662 | 10/1950 | Hipps | 128/92 |
| 3,128,768 | 4/1964 | Geistauts | 128/305 |
| 3,298,261 | 1/1967 | Lynn | 81/185 |
| 3,682,177 | 8/1972 | Ames et al. | 606/80 |
| 3,835,858 | 9/1974 | Hagen | 128/305 |
| 4,218,794 | 8/1980 | Seidel | 7/138 |
| 5,030,222 | 7/1991 | Calandruccio | 606/96 |
| 5,351,586 | 10/1994 | Habermehl | 81/438 |
| 5,409,493 | 4/1995 | Greenberg | 607/79 |
| 5,505,737 | 4/1996 | Gosselin et al. | 606/80 |
| 5,554,154 | 9/1996 | Rosenberg | 606/80 |
| 5,667,509 | 9/1997 | Westin | 606/80 |

FOREIGN PATENT DOCUMENTS

| | | |
|---|---|---|
| 1566114 | 10/1970 | Germany . |
| 3800482 | of 1989 | Germany . |
| 2022495 | 12/1979 | United Kingdom . |

OTHER PUBLICATIONS

Surgical Instruments Appliances & Hospital Equipment, 1930 edition (Allen & Hansburys Ltd) "Fracture Operation Instruments". pp. 590–593, Apr. 1931.

*Primary Examiner*—Michael Buiz
*Assistant Examiner*—Lien Ngo
*Attorney, Agent, or Firm*—Webb Ziesenheim Lodgson Orkin & Hanson, P.C.

[57] ABSTRACT

A driver for use in orthopedic surgery having a generally elongate housing adapted for single-handed gripping operation. The driver includes an engagement mechanism associated with the housing for releasably engaging the proximal end of a longitudinally extending driven member and includes a driven member, such as a flexible drive spindle, for rotatably driving the engagement mechanism. The driver further includes shield that is supportingly connected with an end of the housing so as to extend co-axially with and fully circumscribe the driven member. The distal end of the shield terminates in an end portion adapted to be placed against a surface of a body part into which the member is driven. The driver also includes a mechanism to permit relative movement in an axial direction between the engagement mechanism and the end portion for advancement into and retraction from the surface so that, in use, single-handedly, the driven member is always fully shielded and supported. In the preferred form of the invention the relative movement between the engagement mechanism and end portion is achieved by a longitudinally retracting shield. In other embodiments the shield is fixed and the engagement mechanism is advanced internally within the housing.

32 Claims, 12 Drawing Sheets

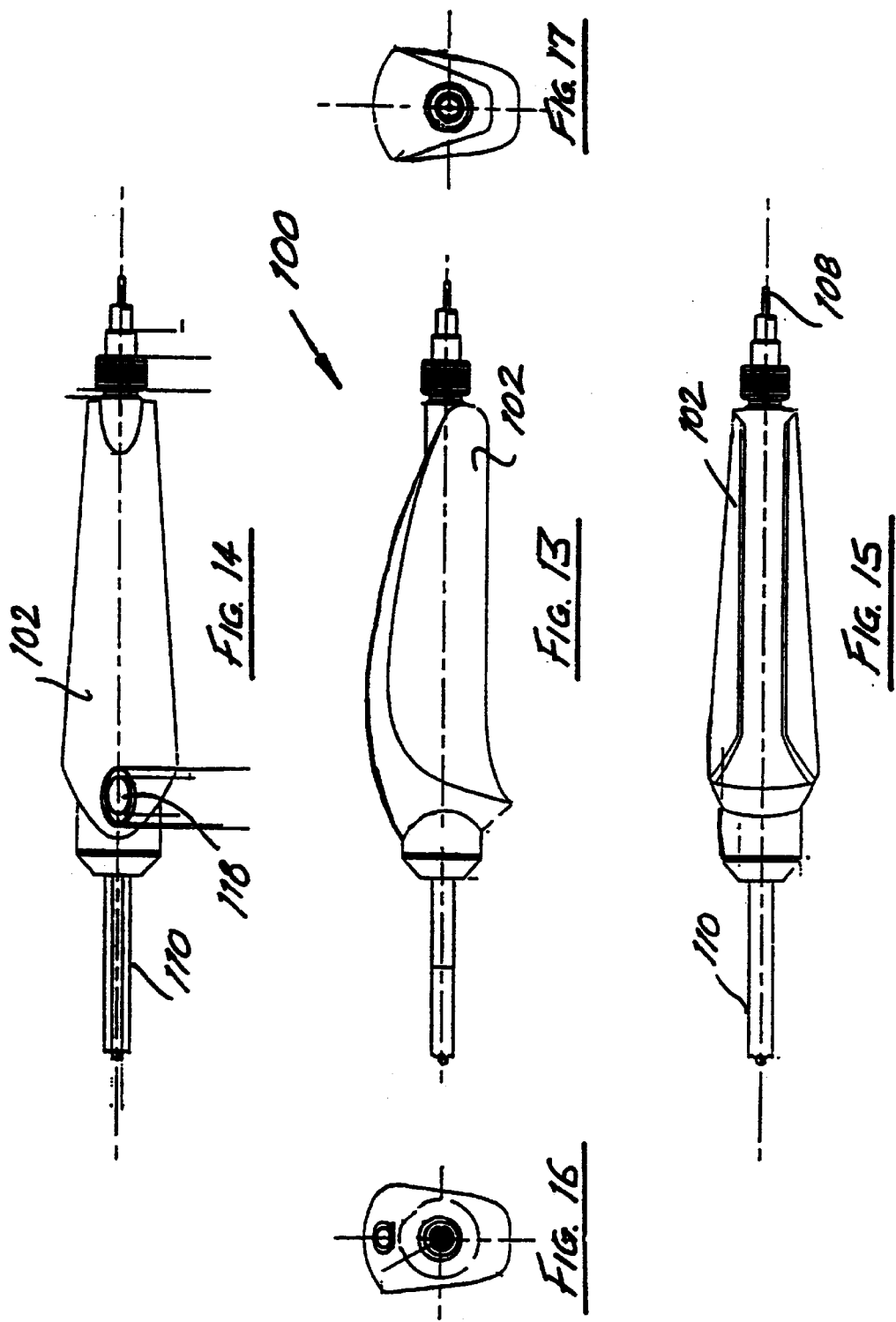

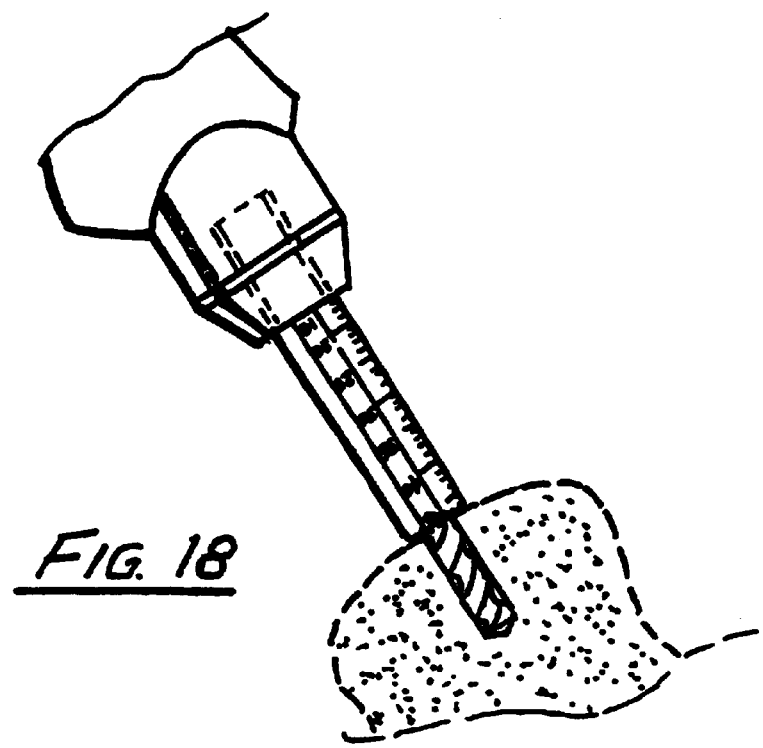
Fig. 18
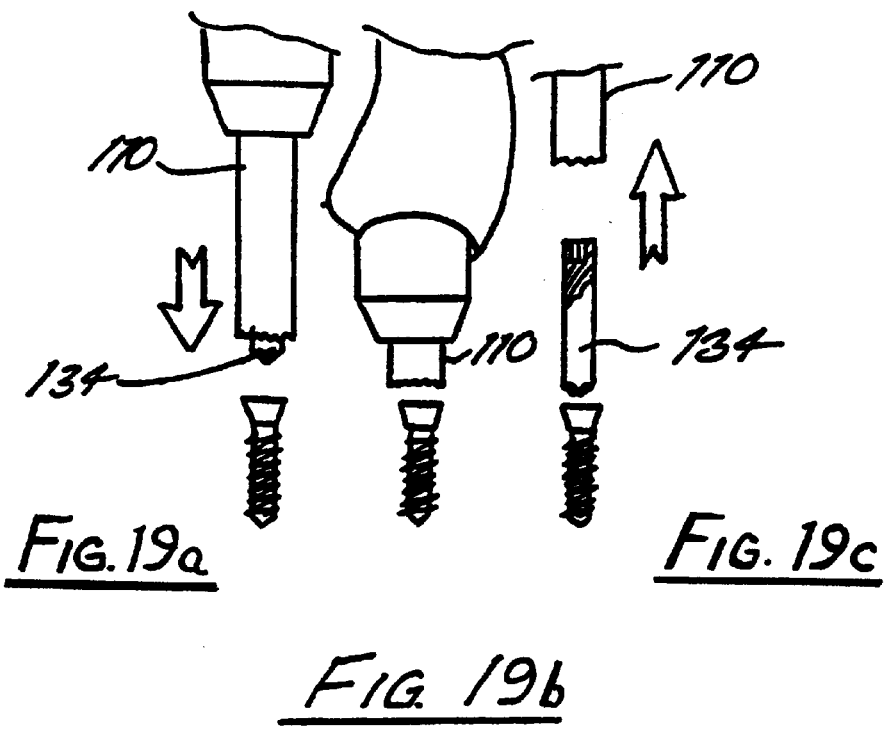
Fig. 19a    Fig. 19c
Fig. 19b

DRIVER

FIELD OF THE INVENTION

The present invention relates to a single handed power driver with integral shield mechanism for drilling and inserting fasteners such as screws and the like.

The invention has been developed primarily for use in orthopaedic surgery and will be described hereinafter with reference to this application. However, it will be appreciated that the invention is not necessarily limited to this particular field of use.

BACKGROUND OF THE INVENTION

Orthopaedic surgery often involves the joining of two or more segments of a bone. This join is usually accomplished by bolting, screwing or wiring the segments directly together, or bolting, screwing or wiring the segments to a common plate or other intermediate joining member. It is normally necessary to use some form of powered driver to drive a drill bit, screws, Kirschner wire or other device or implement into the bone to facilitate the join.

The positioning of the bolts, screws or wires in the bone is extremely critical for the integrity of the joint and the subsequent healing process. Accordingly, in addition to the usual complications and stress generally associated with overall patient well being in surgery, the orthopaedic surgeon also has to ensure the driver is very accurately positioned. This is difficult as it often requires holding the bone segments to be fixed in an exact orientation whilst simultaneously aiming, supporting and operating the driver.

To assist in overcoming these problems, a separately supportable drill guide plate or similar is initially positioned adjacent the bone or prosthesis being drilled in order to ensure that the drill bit or similar passes into the bone at the desired location and on the desired course. Ideally, the guide plate also serves to minimise damage to the soft tissue surrounding the bone which may get caught by the rotating drill bit, screw or wire.

It will be appreciated that the above procedure requires the surgeon to hold in position the fragments to be fixed whilst simultaneously using the power drill and positioning and holding the drill guide. Clearly, this is something that is difficult, if not impossible to achieve with any accuracy with only two hands, so often the surgeon has to depend on the help of an assistant. However, this is not only labour intensive but is rarely satisfactory, as the assistant is not generally in a position to maintain or judge correct alignment and their presence may even restrict access to and/or sight of the surgical opening.

To further complicate matters, the prior art procedures often require use of a separate tool to increase and/or determine the depth of travel of the drill or other driven member.

It is an object of the invention to overcome or at least ameliorate one or more of these deficiencies of the prior art or at least offer a useful alternative thereto.

DISCLOSURE OF THE INVENTION

According to a first aspect of the invention there is provided a compact single unit driver with integral shield device for use on a body or body part in orthopaedic surgery or the like, the driver including:

a housing adapted for single handed gripping operation;

engagement means associated with said housing for releasably engaging the proximal end of a longitudinally extending driven member;

drive means for rotatably driving the engagement means;

longitudinally extending generally supporting non rotating shield means connected with an end of the housing so as to extend co-axially with and circumscribe said driven member, the distal end of said shield means terminating in an end portion adapted to be placed against a surface of the body part into which or toward which the member is to be driven; and means to permit relative movement in an axial direction between said engagement means associated with said housing and said end portion for advancement into or toward said surface or body part and retraction therefrom so that, in use, single handedly, the rotating engagement means and portion of said driven member above said surface of said body part are always fully shrouded by means of the housing and/or the shield means.

By reference herein to an integral shield device it is meant simply that the shield device forms a permanent part of the driver as a whole. As such the shield need not necessarily be integrally formed with the housing, but may be separately manufactured and captively retained in a suitable manner.

Desirably, the shield means is sized to also act as a guide for the driven member. However, in some embodiments the shield means may include separately identifiable guide means at or adjacent the end portion of the shield.

The driven member may be a drill bit, screw, Kirschner wire or other surgical implement, tool or device. Preferably, the device is configured such that the distal point of the driven member in the inoperative mode protrudes slightly from the shield means to facilitate accurate positioning prior to driving and is, ideally, retractable, relative to the end portion, prior to operation.

The driven member may directly engage the engagement means such as in the case of a drill bit. Alternatively the driven member may engage an intermediate member that directly attaches to the engagement means such as in the case of an intermediate bit to engage a screw.

In a first preferred form of the first aspect, the engagement means are generally fixed relative to the housing and the shield means are retractable into said housing as the driven member is advanced into the surface. Preferably, the shield means is retractable against a biasing means such that as the driven member is advanced or retraced by movement of the housing, the shield means is urged into maintained contact against the surface into which the member has been driven. In another form, the shield means comprises two or more cylindrical concentric telescoping portions that decrease in diameter towards the end portion.

Desirably, in this first preferred form the shield means comprises a generally cylindrical member, which, preferably, is marked externally with gradations indicative of the penetration depth of the driven member beyond the shield end portion. In another preferred form the depth indication is provided via a direct window on the housing or via a display coupled to an electronic displacement transducer.

This first embodiment provides an elegantly simple solution to the prior art problems, enabling the driver to be advanced by applying a linearly acting driving force to the housing which drives in the member and simultaneously overcomes the biasing force on the shield. In this manner the drill can be accurately positioned and guided and the soft surrounding tissues protected from damage by the shield, the retraction of which also directly or indirectly provides an indication of depth of penetration. All this is achieved with a compact unit that requires only one handed operation.

According to a second embodiment of the first aspect of the invention, the shield means is rigidly connected to or forms part of the housing and the engagement means are adapted to move internally relative to the housing between a retracted position in which the driven member is substantially located within the shield means and an extended position in which a part of the driven member protrudes from the shield means as it is driven into the surface.

In this second embodiment a plurality of changeable shield portions may be provided for use with the driver. The bore of the guide means in each of the shield means may be produced in one of a range of diameters to receive different diameter driven members. A supporting clearance fit is generally provided between the bore of the guide and the driven member. However, in some cases where the driven members have sufficient rigidity, one shield of, for example, 4.5 mm internal diameter is suitable for use with all drills and wires under, say, 4.0 mm.

In both embodiments, the drive means preferably includes a first motor which is desirably electrically or pneumatically powered. The first motor may be internal or external the driver. Preferably, in the first embodiment the motor is external.

In one variation of the second embodiment the driver includes a telescopic coupling operatively connecting an internal first motor to the engagement means. In this embodiment the motor is fixed relative to the shield means and the engagement means travels along the rotational axis of the driven member to move the driven ember between the retracted and extended positions. In another variation of the second embodiment the internal first motor and the engagement means travel along the rotational axis together.

Alternatively, in either embodiment, the first motor may be external the drill with a flexible coupling, such as a cable drive, operatively connecting the first motor to the engagement means.

The first motor may, in the second embodiment, be adapted to both rotationally drive the engagement means and extend and retract the engagement means and hence the driven member.

In an alternative arrangement of the second embodiment the first motor drives the engagement means only and a second motor is adapted to extend and retract the drill bit.

The drill of the second embodiment may include gear means operatively connected to the any or all of the motor or motors or engagement means for extension and retraction of the engagement means. The gear means may include selectively operable advancement and retraction gears for extending and retracting the engagement means. In other embodiments a single gear is used with a bidirectional motor.

In further variations of the second embodiment the engagement means may be advanced and retracted manually.

Optionally, means can also be provided to give an external indication as to travel of the engagement means which in this second embodiment is indicative of depth of penetration of the driven member.

The driver may also include a variable speed gearbox between the first motor and the engagement means. Alternatively the first motor may be a variable speed motor. If desired, the first motor also provides a fixed slow speed. In all embodiments the engagement means is preferably a female/male connector adapted to engage a corresponding male/female connector provided on the driven member. The engagement means can also include other types of connectors such as snap-lock fittings or chucks.

In one form the female connector and the proximal end of the driven member preferably include a recess and a correspondingly shaped spigot respectively. In other embodiments the recess and spigot have square, triangle, hexagonal or star shaped cross sections. The recess and spigot may, alternatively, include mating threads.

The driver may also include a plurality of different sized engagement means to cater for different sized driven members. In an embodiment the driver includes a magazine adapted to hold a plurality of driven members having commonly sized drive head portions, the magazine being adapted to permit rapid engagement of the individual driven members with the engagement means. Desirably, the magazine holds a plurality of like driven members of different size or a selection of different complementary driven members.

In one version of the second embodiment, the driver housing, which is attached to or includes the shield and optional guide portion, is adapted to encase the engagement means. The housing preferably includes external manual controls for the driven member rotation, advancement and retraction of the driven member. The manual controls are preferably positioned on the housing for left or right hand manipulation. The driver may alternatively or additionally include remote controls.

The driver may be configured such that the driven member extends and remains in contact with the surface a short distance from the end portion so as to permit the driven member to engage the surface and thereafter drive itself into the surface. This configuration is applicable when the driven member is, for example, a self tapping screw which, when rotated, will continue to advance itself after initial engagement is made with the surface.

The driver may also be configured to continually advance the driven member into the surface. This configuration is applicable when the driven member is, for example, a drill bit which needs to be both rotated and advanced to drive it into the bone or similar surface.

Desirably, the end portion of the shield includes means, such as serrations or spikes, to help prevent the tip of the driver from "wandering" once in contact with the relevant surface.

In one preferred form the driver is provided with a plurality of driven members of various type and size each having at their proximal ends a common sized and shaped head portion for engagement with correspondingly sized drive coupling forming the engagement means on the driver.

In another preferred form the driver is provided with one or more adaptors for driven members, each adaptor comprising at one end a standard sized and shaped head portion for engagement with a correspondingly sized drive coupling forming the engagement means on the driver, said adaptor being configured at said other end remote said first end for torque transmitting attachment to a driven member of a given size.

Preferably, the adaptor is made of a plastics material or the like, the torque transmitting attachment to said driven member being achieved, for example with drill bits, by moulding onto an end of said driven member that either incorporates a driving flat or has been flattened or roughened to reduce the likelihood of rotation within the adaptor. In the case of screws or the like, the torque transmitting attachment is via a suitable shaped drive portion selected to correspond with the drive recess provided in the head of the screw.

Desirably, the head portion of the second and third aspects is a standard shape such as round, hexagonal, square, d-shaped or the like. With the round head portion a standard chuck may comprise the drive coupling. In the other variations where the head portion may have a square or hexagonal cross section, it is preferable the drive coupling is correspondingly sized and shaped.

Preferably, the driver according to the first aspect of the invention includes an engagement means sized and configured to receive driven members according to the second aspect of the invention or driven members incorporating adaptors according to the third aspect of the invention.

Desirably, the driver is of a general pencil-style shape. However, other configurations, including a pistol-style arrangement, are possible.

BRIEF DESCRIPTION OF THE DRAWINGS

Preferred embodiments of the invention will now be described, by way of example only, with reference to the accompanying drawings in which:

FIG. 13 is a side view of the driver shown in FIG. 11;

FIG. 14 is a top plan view of the driver shown in FIG. 13;

FIG. 15 is an inverted plan view of the driver shown in FIG. 13;

FIG. 16 is a front end view of the driver shown in FIG. 13;

FIG. 17 is a rear end view of the driver shown in FIG. 13;

FIG. 18 is a part view of the driver shown in FIG. 11 illustrating the shield in the retracted position during use;

FIGS. 19a–c are schematic representations of how the retractable shield driver operates with a screw and intermediate drive adaptor;

PREFERRED EMBODIMENTS OF THE INVENTION

Preferred embodiments of fixed shield drivers according to the invention will now be described with reference to FIGS. 1 to 10 of the accompanying drawings.

Figure 1:
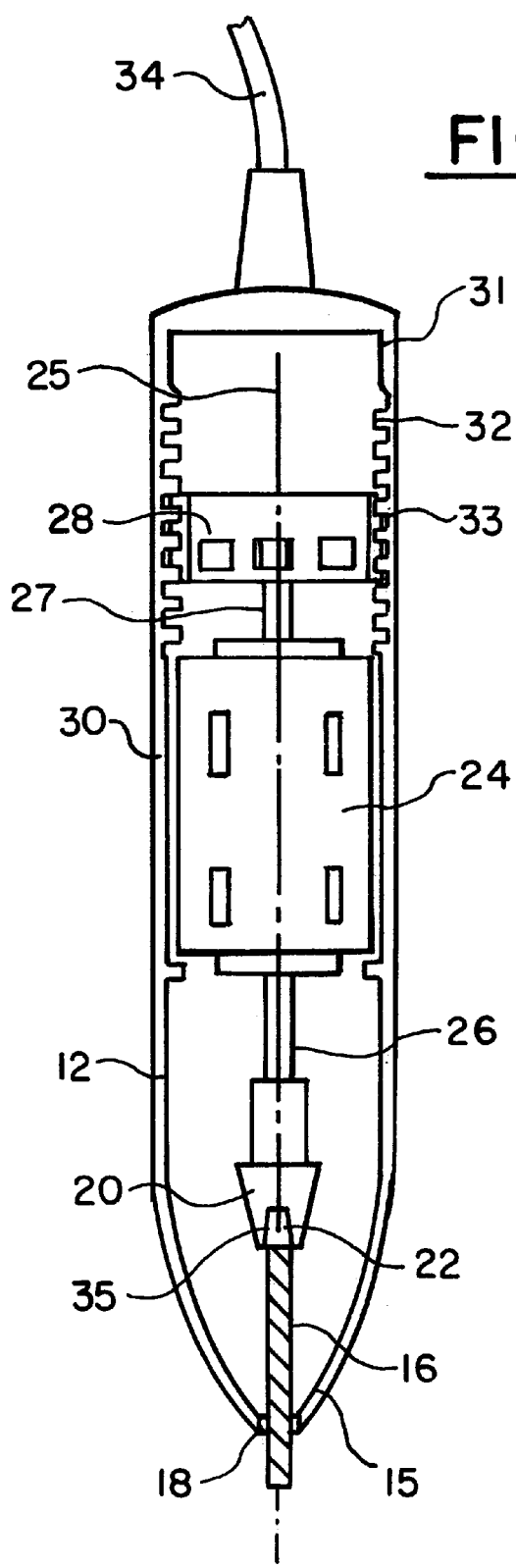
FIG. 1 is a first embodiment of a fixed shield driver according to the first aspect of the invention with the driven member in the extended position.
Figure 2:
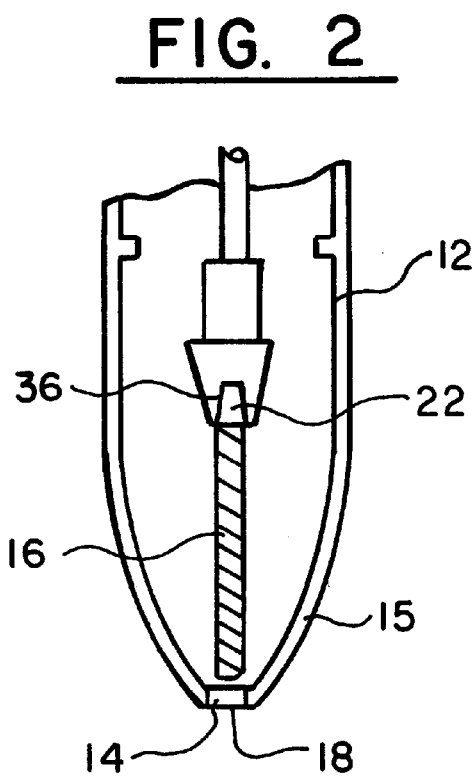
FIG. 2 is a partial view of the driver shown in FIG. 1 with the driven member in the retracted position.

Referring firstly to FIGS. 1 and 2, there is shown a preferred pencil-style driver 10 for use in orthopaedic surgery or the like. The driver includes a shield 12 having a bore 14 surrounded by an adjacent guide portion 15 of the shield 12 sized and adapted to receive a driven member in the form of drill bit 16. The guide portion terminates in a distal end portion 18 which is adapted to be placed against the surface into which the drill is to be driven. The driver 10 also has an engagement means in the form of female connector 20 for releasably engaging the driven end 22 of the driven member 16.

A drive means, in the form of electric motor 24, is used to rotate the engagement means 20 and drill bit 16. The connector 20 is coupled to the motor 24 by a drive shaft 26. The drive shaft 26 is rotated by the motor 24, and is also able to slidably pass through motor 24 in the direction of longitudinal axis 25. The end 27 of the drive shaft opposite the connector is connected to second motor 28.

The driver has a generally cylindrical body 30 of which shield 12 forms an integral part. The distal end 31 of the body 30 contains an internal gear form 32 adapted to engage the external gears 33 of the second motor 28.

The bore 18 of the guide portion 15 of the shield 12 is sized as a clearance fit around the outer diameter of the drill bit 16. A number of interchangeable shields 12 having correspondingly sized bores are provided to accommodate various sizes of drill bits, screws, wire or the like. However, depending on the stiffness of the driver members, one shield/guide size may be adequate for a range of driven members.

The female connector 20 includes a recess 35 and the proximal end 22 of the drill bit has a correspondingly shaped spigot 36. In this embodiment the recess and spigot have a square cross-section. It will be appreciated that various other cross-sections may be used and they may include snap-lock fittings or similar to provide a secure releasable connection between the connector and the drill bit.

The body 30 also includes external manual controls (not shown) to allow the surgeon to control the speed of the drill bit rotation, advancement and retraction. Remote controls, such as foot pedals (not shown) are also available for use with the driver 10. Electrical power for the driver is supplied through a cable 34.

In use, the spigot 36 of the drill bit is inserted into the recess 35 of the connector 20. The second motor 28 is then used to position the engagement means such that the distal end 18 of the drill bit is within the guide portion 15. This is achieved by energising the second motor 28 and thereby rotating the gears 33 causing the second motor to travel in the direction of the axis 25. As the drive shaft length is fixed, the translational travel of the second motor 26 results in identical translational travel of the female connector 20 and the drill bit 16. The end 18 of the guide portion is then placed adjacent the bone or other apparatus into which the surgeon intends to drive the drill bit. The surgeon then uses the first motor 24 to rotate the drill bit and the second motor 26 to advance it from within the guide and extend the drill bit into the bone or other surface.

The driver according to the invention obviates the need for the surgeon to manipulate and position a separate guide plate and therefore provides a simplified surgical procedure with more accurate positioning of the drill bit or the like. In particular, the driver allows accurate positioning of the drill bit whilst still providing a shield and/or guide so as to overcome the difficulties associated with driving through soft tissue and the like.

If a screw is driven instead of a drill bit, then an intermediate member (not shown) may be needed which has one end adapted to connect to the connector 20 and another adapted to releasably engage the screw head.

Figure 3:
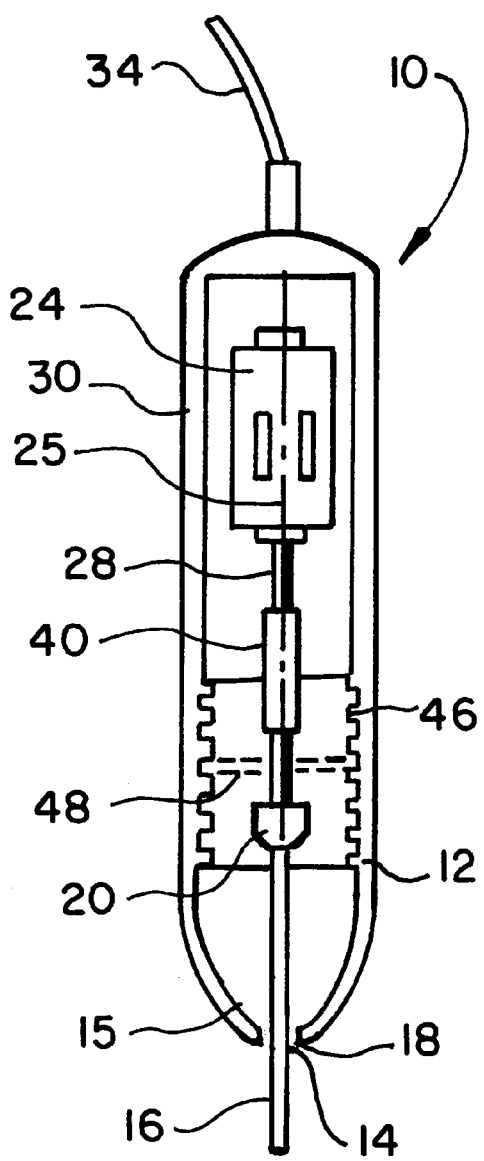
FIG. 3 is a sectional side view of a second embodiment of a fixed shield driver according to the first aspect of the invention.
Figure 4:
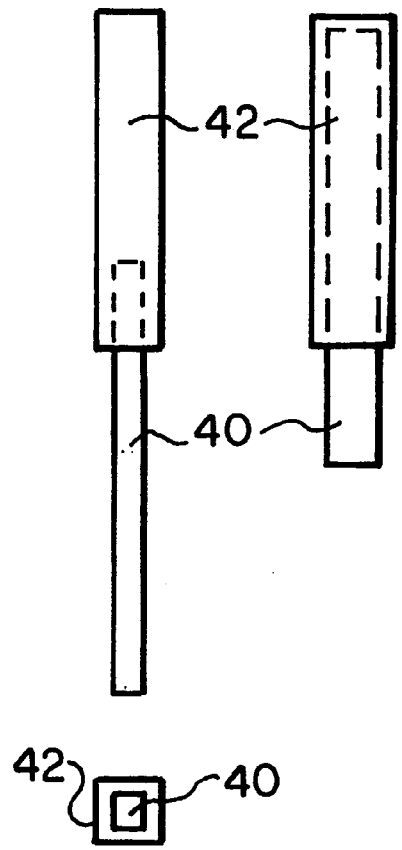
FIG. 4 is an enlarged view of a telescopic coupling used in the driver of FIG. 3 in extended and retracted positions.

FIGS. 3 and 4 show a second embodiment of a fixed shield driver according to the invention in which like numerals will be used to designate corresponding features.

In this embodiment, a telescopic coupling 40, comprised of square cross-section inner and outer portions 40 and 42 respectively, is connected to the drive shaft 28 intermediate the motor 24 and the connector 20. Internal gears 46 are provided in the body 30 forward of the motor and are engaged by a worm gear 48 attached to the drive shaft. In this way, rotation of the drive shaft by the motor 24 causes the drill bit 16 to rotate about the axis 25 and also translate along the axis 25 as the worm gear 48 is driven along the gears 46. The movement of the connector 20 relative to the motor 24 is accommodated by the telescopic coupling 40, as exemplified in the two extreme positions shown in FIG. 4. The pitch of the gears 46 permits optimisation of the relationship between the rotational speed of the drill bit and its translational advancement and retraction into the bone or other surface.

Figure 5:
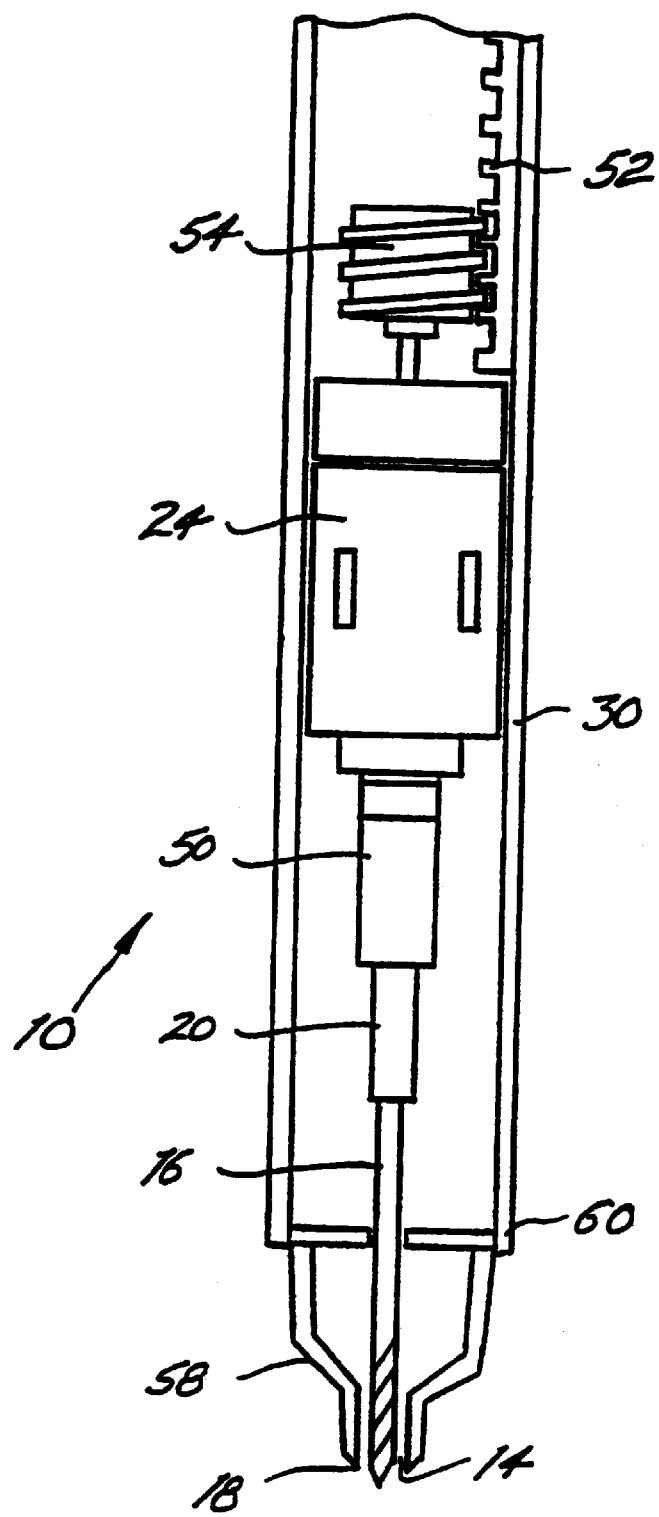
FIG. 5 is a partial sectional side view of a third embodiment of a fixed shield driver according to the first aspect of the invention.

Turning now to FIG. 5 there is shown a third embodiment of a fixed shield driver according to the invention in which like numerals will again be used to designate corresponding features.

In this embodiment, the distance between the first motor 24 and the connector 20 is fixed by coupling 50. The body 30 includes an internal rack gear 52 engaged by a worm gear 54 coupled to second motor 26. The second motor is mounted to the rear of the first motor 24.

Rotation of the worm gear 54 causes it to travel along rack 52, simultaneously translating the first and second motors, the connector 20 and the drill bit 16.

The third embodiment of the fixed shield driver according to the first aspect of the invention also includes a replaceable stepped guide portion 58 which is a press or snap lock fit into the distal end 60 of driver body 30.

Figure 6:
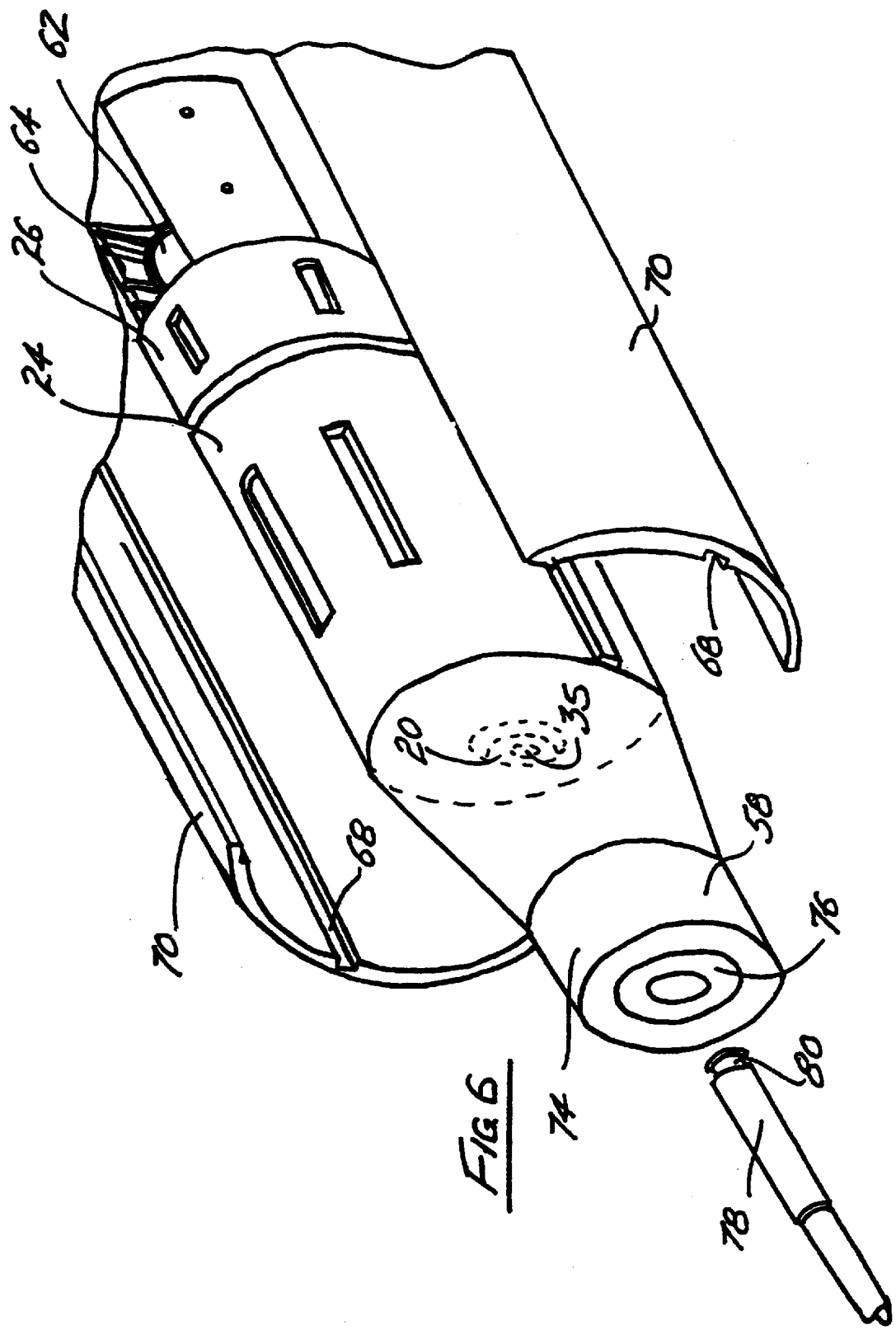
FIG. 6 is an exploded perspective view of a fourth embodiment fixed shield driver according to a first aspect of the invention.

A fourth embodiment of fixed shield driver is shown in FIG. 6. This embodiment also includes a second motor 26 coupled to the rear of first motor 24 and uses a worm gear 62 to advance and retract the motor along gears 64. The external circumference of the drive motor 24 is provided with ridges 66 which are configured to slide along correspondingly shaped recesses 68 provided in the two halves of the drill body 70 and 72. This embodiment also includes a stepped guide 74 with a replaceable bore section 76. The replaceable bore section 76 allow the internal diameter of the guide bore to be altered whilst leaving the guide itself in place. The drill bit 78 includes an annular recess 80 adapted to snap lock into the connector 20.

Figure 7:
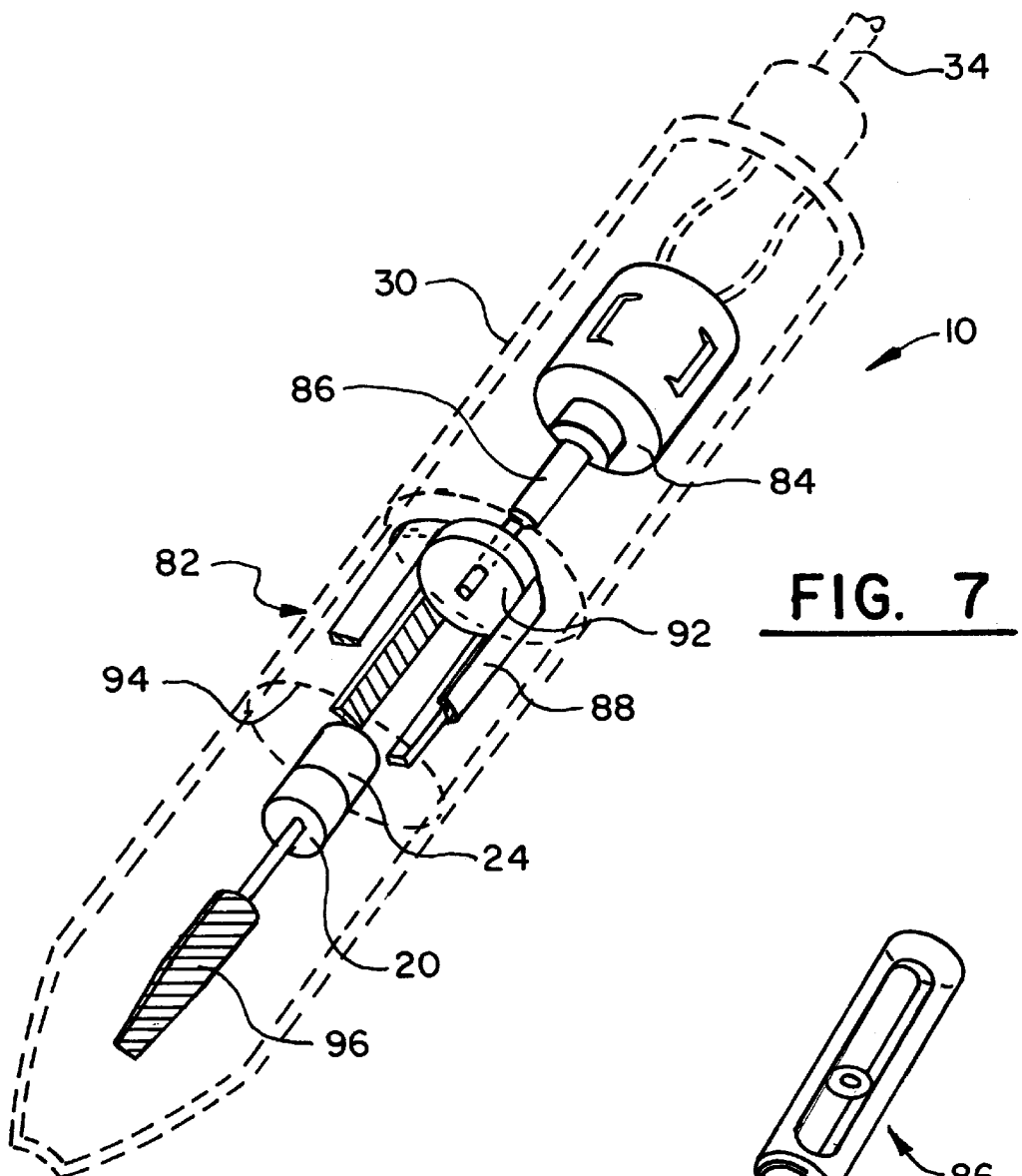
FIG. 7 is an internal perspective view of a fifth embodiment fixed shield driver according to a first aspect of the invention.
Figure 8:
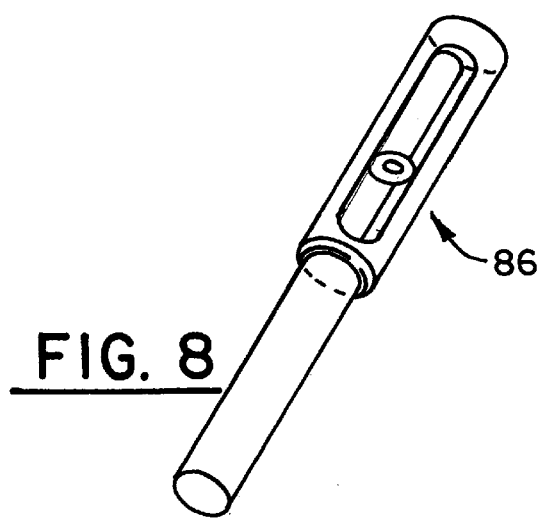
FIG. 8 is a telescopic coupling for use with the driver shown in FIG. 7.
Figure 9:
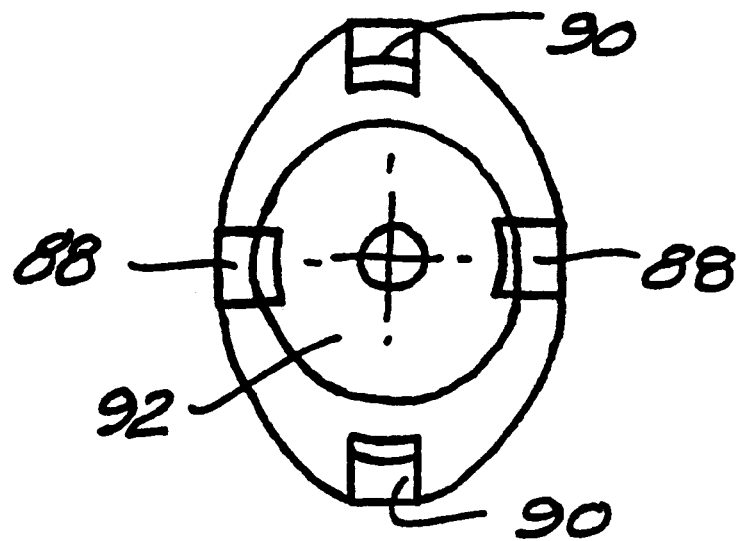
FIG. 9 is a diagrammatic end view of a gear assembly for use with the driver shown in FIG. 7 with the advancing gears engaged.

Turning now to FIGS. 7 and 8 there is shown the internal components of a fifth embodiment fixed shield driver encased by the driver body 30 shown in phantom. In this embodiment, the first motor 24 is directly attached to the end of the connector 20. The other end of the motor is fixed in relation to a gear mechanism 82 connected to a second motor 84 by a telescopic coupling 86. The gear mechanism 82 includes an opposed pair of advancement gear racks 88 and an opposed pair of retraction gear racks 90.

The second motor 84 rotates the worm gear 92 which can be selectively engaged by one of the opposed pairs of gear racks 88 or 90. The racks are surrounded by a spring steel casing 94, best shown in FIGS. 9 and 10, which deforms under digital pressure to bring one of the gear sets into engagement with worm gear 92.

Figure 10:
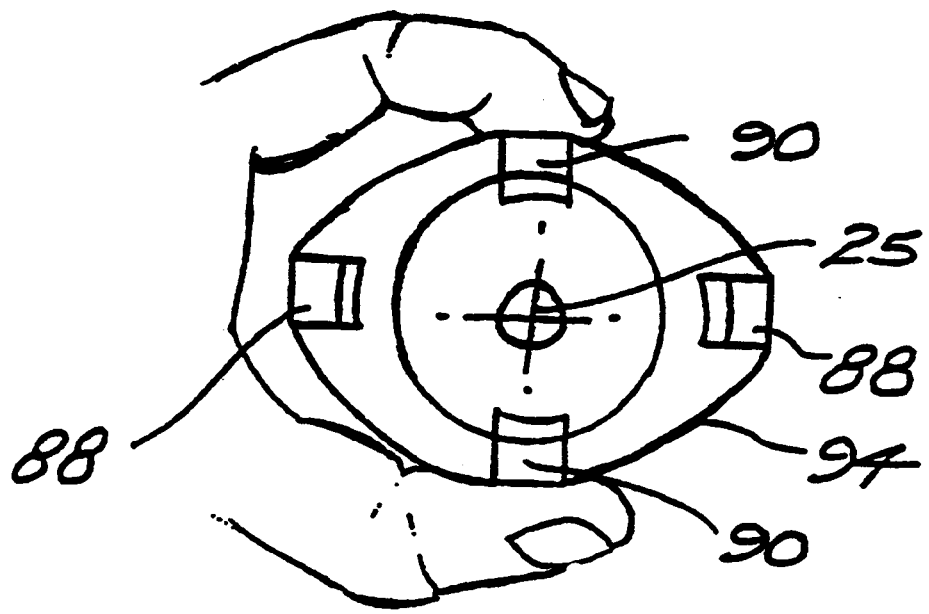
FIG. 10 is a diagrammatic cross-sectional end view of the gears shown in FIG. 9 with the retraction gears engaged.

As shown in FIG. 10 when digital pressure is applied to the retracting gear set 90 they are brought into engagement with worm gear 92 and rotation the worm gear causes the first motor, the connector and a tap 96 to retract into the shield 12.

Similarly, if the advancement gear tracks are pressed into engagement with worm gear 92 then the same directional rotation of the motor will cause the first motor 24, the connector 20 and the tap 96 to advance and protrude from the end of the guide.

In a variation of this embodiment only a single opposed pair of gear racks are used and a switch is provided to reverse the direction of the second motor 26 in order to selectively advance or retract the connector 20 and associated equipment.

In further embodiment of the driver (not shown) the motor is fixed relative to the connector and is able to be manually translated within the drive body. This embodiment has particular application in the driving of self-tapping screws and the like which advance themselves into the bone after initial engagement is made as the connector and accompanying motor are drawn forward by the screw due to the self-tapping action.

A preferred embodiment of the retractable shield driver according to the first aspect of the invention will now be described with reference to FIGS. 11 to 22 of the accompanying drawings.

The primary difference between this embodiment and those previously illustrated and discussed above, is that no separate mechanism is provided for advancing the engagement means relative to the housing. Instead, the advancement is achieved by applying a linearly acting load to the driver, the shield being configured to retract into the housing as the driven member advances, thereby ensuring that the surrounding soft tissue is protected at all times.

This is a very simple solution that provides excellent feel for the operator as well as providing a direct visual indication of the penetration of the driven member, either directly by means of the retracting shield, or, via a window or electronic indicator on the housing itself These features are described in more detail below.

Figure 11:
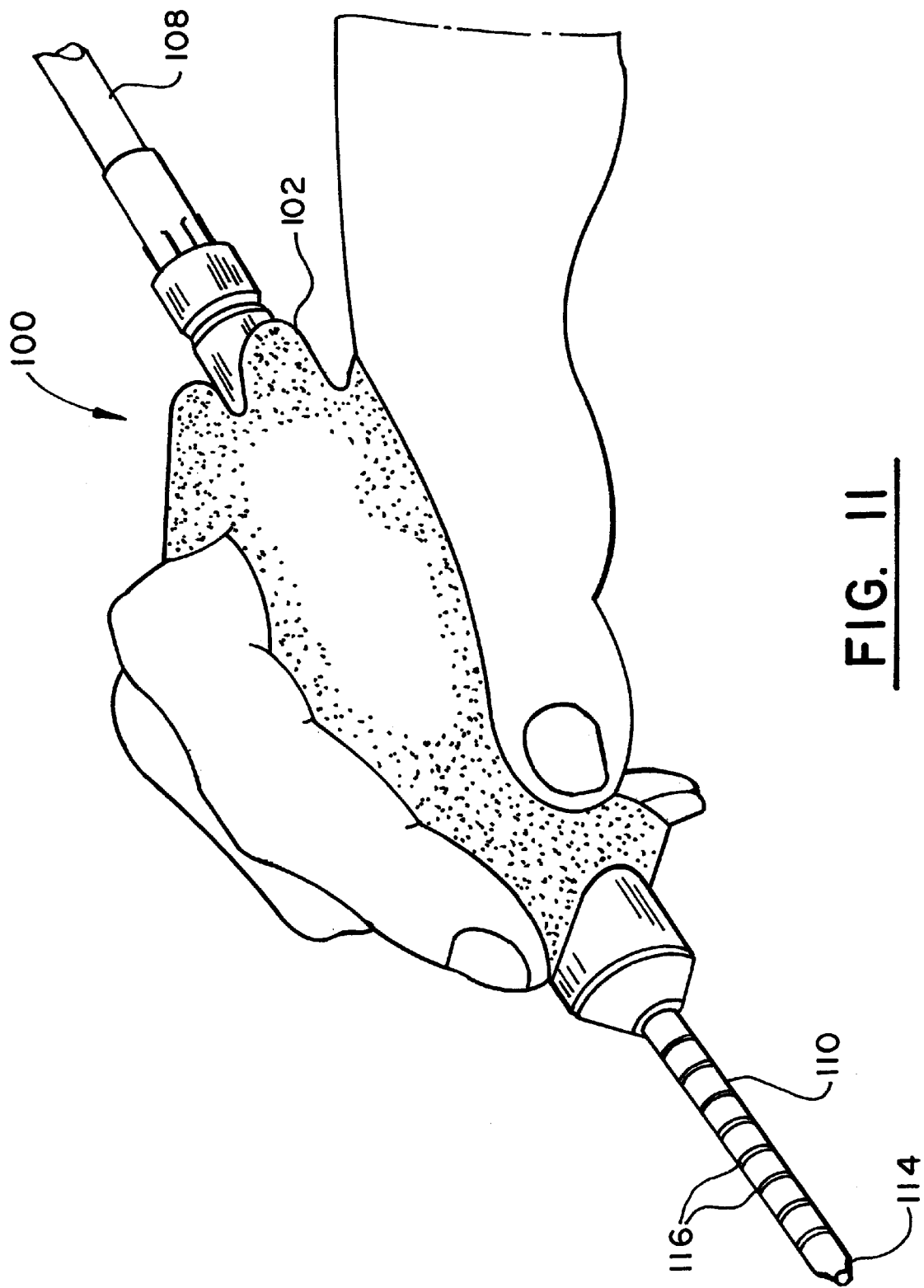
FIG. 11 is a diagrammatic perspective view of a first embodiment retracting shield driver according to the first aspect of the invention.
Figure 12:
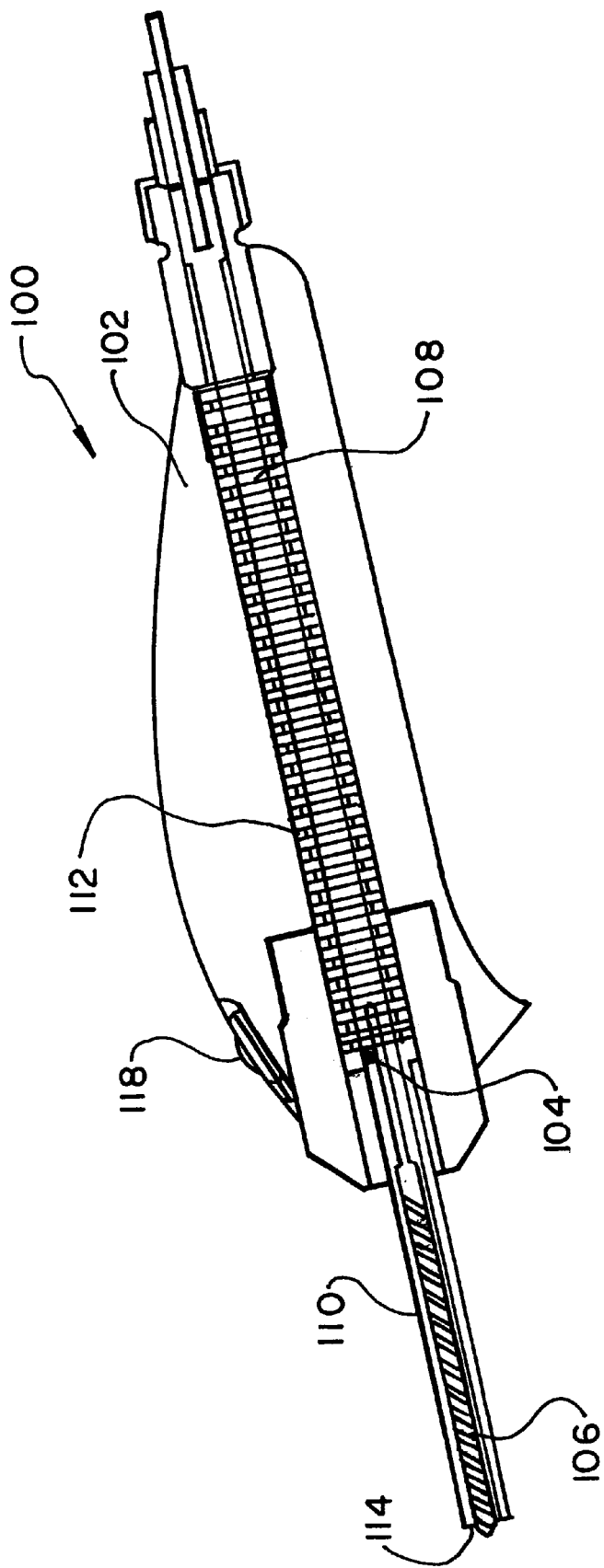
FIG. 12 is a schematic sectional view of the driver shown in FIG. 11.

Turning first to FIGS. 11 and 16, it can be seen that the driver 100 once again has a generally elongate housing 102 that is contoured and otherwise adapted for single handed gripping operation. Engagement means, shown generally at 104, are provided within the housing for releasably engaging the proximal end of a longitudinally extending driven member such as the drill bit 106 shown. Drive means are again provided for rotatably driving the engagement means which, in the embodiments shown comprises a flexible drive shaft 108 which is externally driven by an electrical pneumatic motor 128 (see FIG. 22).

The driver 100 also includes a generally cylindrical retractable shield 110 which is biased outwardly from the housing by means of a captive compression spring 112. The end portion 114 of the shield 110 is preferably serrated or includes spikes thereon to grip the bone surface to be drilled in order to prevent the drill from wandering during use.

In the embodiments illustrated, the generally cylindrical shield 110 is marked with gradations 116, such that as the shield retracts telescopically within the housing 102 the operator is provided with a visual indication as to the effective penetration depth of the drill 106. In other embodiments the depth indication is achieved via a window provided in the housing which shows a marker on the shield 116 retracting into the housing against an appropriate scale. Other more sophisticated versions may include some form of electrical or electronic display responsive to an appropriate displacement transducer.

One preferred shape of the driver housing 102 is shown most clearly in the orthogonal views depicted in FIGS. 13 to 17. In this particular arrangement the button 118 is conveniently located on the upper portion of the housing at or adjacent the location at which the operator's index finger would rest during use. In other embodiments, not shown, the on/off mechanism is remote from the driver housing 102 and may be, for example, foot operated.

Figure 20A:
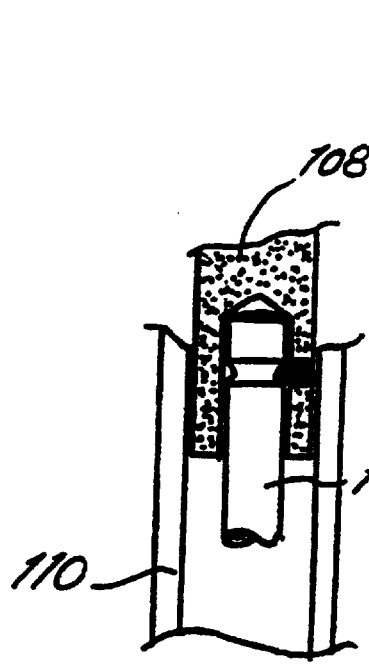
FIGS. 20a–c illustrate examples of quick release drive coupling suitable for use with drivers of the first aspect of the invention and driven members in accordance with the second and third aspects of the invention.
Figure 20B:
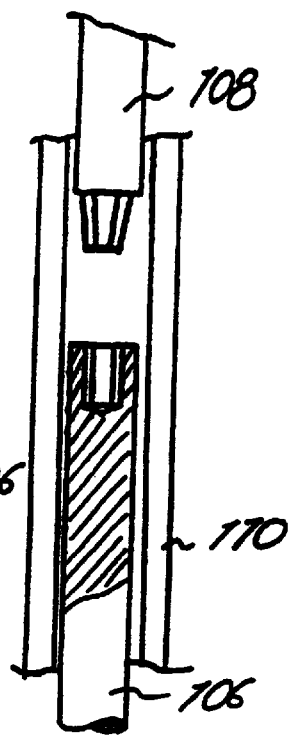
Figure 20C:
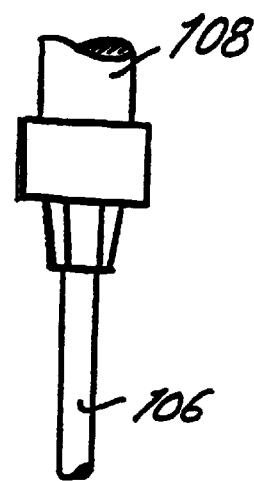

Turning next to FIGS. 20a–c there is shown a range of quick release coupling arrangements suitable for use with various embodiments of the drivers previously illustrated. The left most design illustrates a spring-ball type connector, the centre design shows a tapered hexagonal sectioned male drive and corresponding hexagon female socket; and the right most design shows a standard tapered chuck type coupling.

It will be appreciated that with the previously described retractable shield drivers, either long drill bits or other driven members will be required because of the retraction of the rigid shield 110 into the housing body, particularly if a conventional chuck device is used as the engagement means, or an engagement means must be used which has an overall diameter that is less than the internal diameter of the shield. In the latter case, preferred narrow style engagement means include preferably slightly tapered male driver connectors having appropriate drive flats that are adapted to frictionally engage correspondingly shaped female recesses in the proximal end portions of the driven members.

Figure 21:
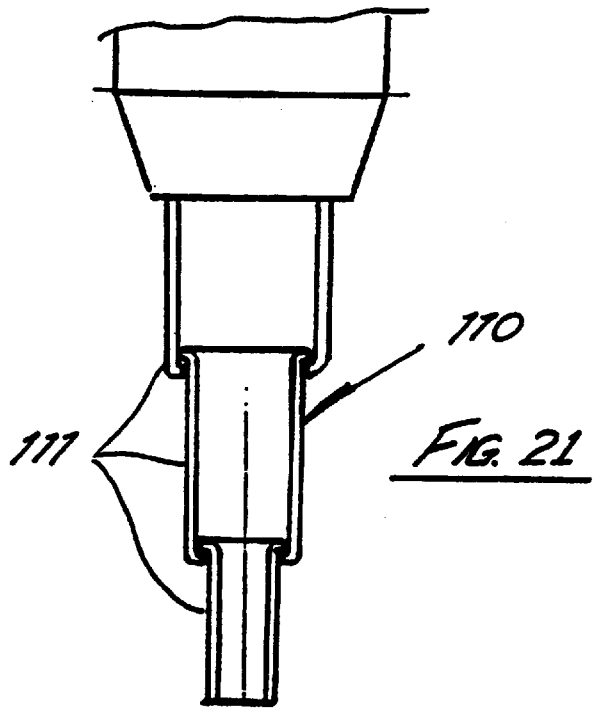
FIG. 21 is a schematic part view of an alternate telescoping shield arrangement for use with the retractable shield driver according to the first aspect in the invention.

These problems are ameliorated in one alternate embodiment by use of a collapsible shield configuration as shown in FIG. 21 which comprises a plurality of telescoping cylindrical portions 111 which progressively nest one within the other as the driver advances against the surface. Accordingly, when the shield is in the fully retracted position, it extends into the housing only a fraction of it's overall extended length, thereby enabling shorter drill bits and the like to be used without placing undue constraints on the overall diameter of the chuck device/engagement means.

Figure 22:
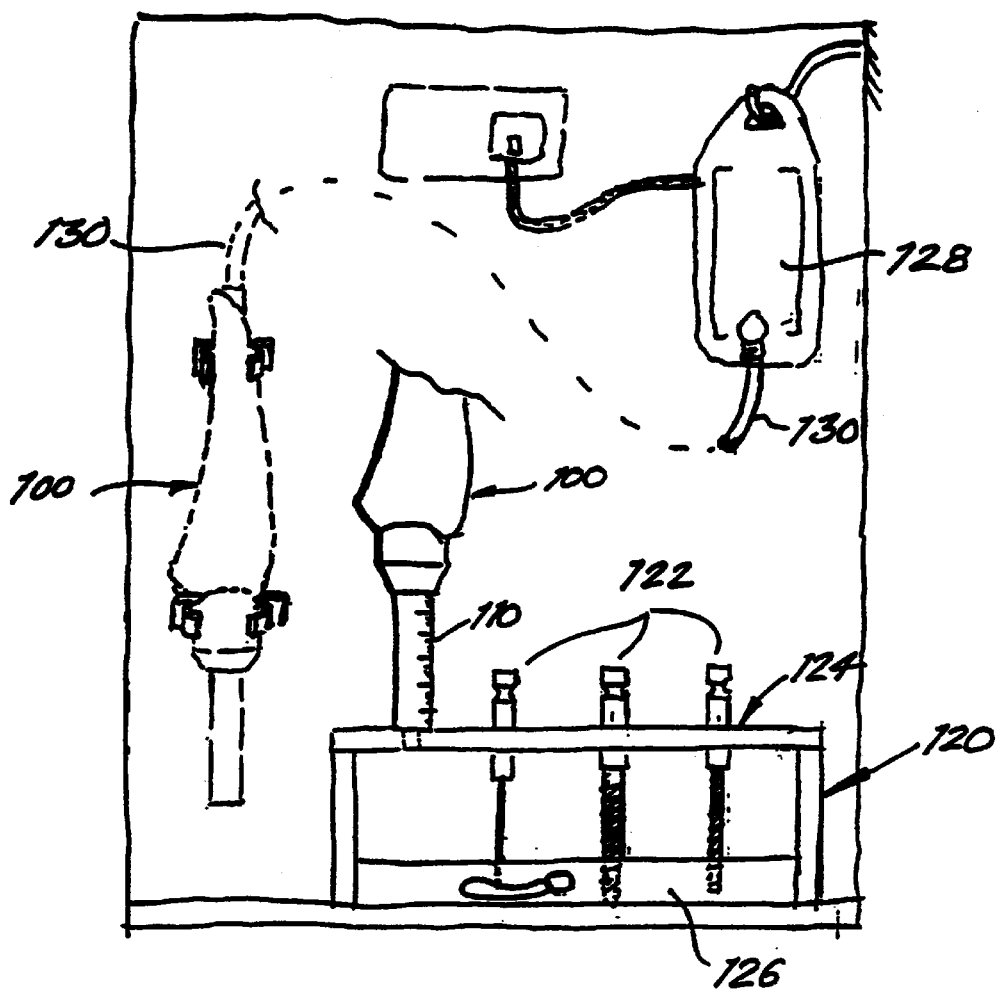
FIG. 22 is a schematic representation of a full driver and driven member kit in accordance with the invention.

Turning next to FIG. 22, there is shown a preferred full driver and driven member kit in accordance with the invention. The kit illustrated includes the retractable shield driver 100 mounted on a support rack 120 adjacent a set of various drilling members 122. The rack includes a fixed upper surface 124 and a selectively releasable gripping mechanism shown generally at 126. Separately mounted at some convenient location is a main drive motor 128 from which extends the flexible drive cabling 130 which attaches to the rear end of the driver 100.

Figure 23:
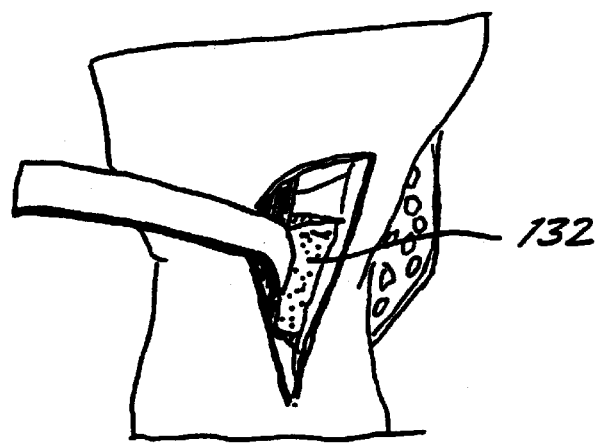
FIG. 23 is a schematic view of a surgical opening made in preparation for a bone chilling operation using the drivers hereinbefore described.

In use, for example, the wound adjacent a bone to be drilled would be opened as shown in FIG. 23. The driver, having been pre-loaded with the appropriate drilling member, would then be taken in one hand and the end of the drill protruding from the end portion 114 would be accurately positioned on the bone 132. The tip of the drill member is then retracted relative to the end portion 114 of the shield 110 by either letting out the shield against the biasing spring from a partially retracted starting position until it hits the surface or alternatively by applying pressure to the driver so that the engagement means 104 retracts a short predetermined distance by a suitable mechanism so that again the end portion 114 comes into contact with the bone.

The driver can then be actuated directly or indirectly and the drill 106 advanced into the bone by applying a linear force to the housing 102. Once the drill has reached the predetermined depth as indicated on the shield or other depth indication device, the driver housing can be retracted, the biasing spring 112 keeping the shield closely adjacent bone at all times thereby preventing the soft tissue from getting entangled in the rotating drill bit (see for example FIG. 18).

In the event that the operation requires a further separate drilling operation or the like be performed, the driver is simply returned to the rack 120 in alignment with a vacant driven member location as shown. Preferably the rack has been configured such that the shield 110 will not be able to pass through the apertures formed in the upper surface 124. This enables the driver to be pushed down in a manner whereby the shield 110 is retracted into the housing 102 and the driven member is exposed. When the distal end of the driven member has been lowered sufficiently, the gripping means 126 (which may comprise any suitable device) is actuated such that the drill bit is firmly held. The driver 100 is then retracted, thereby pulling the drill bit from the quick release coupling. The driver is then advanced to the station that holds the next desired drill member, the drive end of the driven member simply clicking into connection with the engagement means of the driver. First making sure that the gripping mechanism 126 has not been actuated, the driver and newly assembled driven member can then be released from the rack ready for operation. This procedure can be repeated as necessary, making the entire process fast, clean and accurate with no additional assistance being required.

When it is desired to use the driver to insert a screw or the like, an intermediate adaptor 134 is used such as is shown in FIGS. 19a–c. The adaptor has one end adapted for releasable connection to the engagement means and the other adapted for driving the screw.

In the preferred forms of the retractable shield driver according to the invention, a high torque reasonably low fixed speed drive is provided. However, it will be appreciated that other variations are possible with different fixed speeds or variable speed control as maybe required under different circumstances.

In many of the fixed shield embodiments described, the drivers are electrically powered by mains power introduced into the driver along cable 34. However, battery power may be used to reduce the hazard of a power cable trailing the driver during surgery. In other embodiments, particularly the retractable shield embodiments, pneumatic or hydraulic power is used.

Further, whilst generally pencil shaped housing configurations have been described, other embodiments include alternate configurations such as pistol-styled housings.

Although the invention has been described with reference to specific examples, it will be appreciated by those skilled in the art, that the invention may be embodied in many other forms.

What is claimed is:

1. A compact single unit driver with integral shield device for use on a body part in surgery, the driver including:
    a housing adapted for single handed gripping operation;
    engagement means associated with said housing for releasably engaging an end of a longitudinally extending driven member;

drive motor for rotatably driving the engagement means; longitudinally extending non-rotating shield connected with an end of the housing, the shield extending co-axially with and circumscribing the driven member, the distal end of the shield terminating in an end portion adapted to be placed against a surface of the body part toward which the driven member is to be driven; and means to permit relative movement in an axial direction between the engagement means and the end portion of the shield for advancement of the driven member toward the body part and retraction therefrom, wherein in use the engagement means and a portion of the driven member above the surface of the body part are always fully shrouded by the housing and the shield and wherein the driven member in an inoperative mode protrudes from the shield to facilitate accurate positioning prior to use and the driven member is retractable, relative to the end portion, prior to use to allow the end portion to be placed against a surface of the body part prior to use.

2. A driver according to claim 1 wherein the shield means is sized to also act as a guide for the driven member.

3. A driver according to claim 1 wherein the shield includes guide means adjacent the end portion of the shield.

4. A driver according to claim 1 wherein the driven member is selected from the group consisting of a drill bit, a screw, and a Kirschner wire.

5. A driver according to claim 1 wherein the engagement means is fixed relative to the housing and the shield is retractable into the housing as the driven member is advanced through the surface into the body part.

6. A driver according to claim 5 wherein the shield is retractable against a biasing means that urges the shield toward the surface of the body part.

7. A driver according to claim 6 wherein the shield means is retractable against a biasing means that urges the shield means toward the surface.

8. A driver according to claim 7 wherein the shield comprises at least two cylindrical concentric telescoping portions that decrease in diameter towards the end portion.

9. A driver according to claim 5 wherein the retractable shield is marked externally with gradations indicative of the penetration depth of the driven member beyond the end portion.

10. A driver according to claim 5 wherein the depth indication is provided on the housing by an indication means responsive to the retraction of the shield.

11. A driver according to any one of claims 6 to 9 wherein the depth indication is provided directly or indirectly on the housing by a suitable indication means responsive to the retraction of the shield means.

12. A driver according to any one of claims 6 to 11 wherein the drive means comprises a flexible drive powered by a motor provided external to the housing.

13. A driver according to any one of claims 1 to 5 wherein the shield means is rigidly connected to or forms part of the housing and the engagement means are adapted to move internally relative to the housing between a retracted position in which the driven member is substantially located within the shield means and an extended position in which a part of the driven member protrudes from the shield means as it is driven into the surface.

14. A driver according to claim 13 wherein the driver is adapted to receive a plurality of interchangeable shield portions for use with varying sized driven members.

15. A driver according to claim 13 or claim 14 wherein the drive means includes a first motor which is internal or external to the driver.

16. A driver according to claim 15 wherein the driver includes a telescopic coupling operatively connecting an internal first motor to the engagement means, the motor being fixed relative to the shield means and the engagement means being configured to travel along the rotational axis of the driven member to move the driven member between the retracted and extended positions.

17. A driver according to claim 15 wherein the engagement means and an internal first motor travel along the rotational axis together.

18. A driver according to claim 15 wherein the first motor is external to the drill and includes a flexible coupling operatively connecting the first motor to the engagement means.

19. A driver according to claim 15 wherein the first motor is adapted to both rotationally drive the engagement means and to extend and retract the engagement means and hence the driven member.

20. A driver according to claim 15 wherein the first motor rotationally drives the engagement means only and a second motor is adapted to extend and retract the engagement means and hence the driven member.

21. A driver according to anyone of claims 13 to 20 including gear means operatively connected to any or all of the motors or engagement means for extension and retraction of the engagement means.

22. A driver according to claim 21 wherein the gear means includes selectively operable advancement and retraction gears for extending and retracting the engagement means.

23. A driver according to claim 21 utilizing only a single gear in combination with a bidirectional motor.

24. A driver according to any one of claims 13 to 18 wherein the engagement means are adapted to be advanced and retracted manually.

25. A driver according to any one of claims 13 to 24 including means to provide an external reading indicative of depth of penetration of the driven member.

26. A driver according to any one of claims 21 to 25 including a variable speed gear box between the first motor and the engagement means.

27. A driver according to any one of claims 15 to 25 wherein the first motor is a variable speed motor.

28. A driver according to any one of the preceding claims wherein the engagement means is in the form of a chuck device adapted to receive a variety of sizes of driven members.

29. A driver according to any one of claims 1 to 27 wherein the engagement means is preferably a snap-lock type or friction style connector adapted to receive driven members having commonly sized and shaped proximal end portions.

30. A driver according to any one of the preceding claims wherein the end portion of the shield includes a spike means to engage the surface into which the driven member is to be driven so as to prevent the driver from wandering.

31. A driver according to any one of the preceding claims in combination with a plurality of driven members of various type and size each having at their proximal ends a common sized and shaped head portion for engagement with a correspondingly sized drive coupling forming the engagement means of said driver.

32. A driver according to any one of claims 1 to 30 in combination with one or more adaptors for driven members, each adaptor comprising at one end a standard sized and shaped head portion for engagement with a correspondingly sized drive coupling forming said engagement means of said driver, said adaptor being configured at said other end remote said first end for torque transmitting attachment to a driven member of a given size.

* * * * *